(12) United States Patent  
Wu et al.

(10) Patent No.: US 7,321,037 B2
(45) Date of Patent: Jan. 22, 2008

(54) PHOTOSENSITIZER DYE

(75) Inventors: Chun-Guey Wu, Hualien County (TW); Chia-Yuan Chen, Chiayi (TW); Shi-Jhang Wu, Taipei County (TW)

(73) Assignee: National Central University, Taoyuan (TW)

( * ) Notice: Subject to any disclaimer, the term of this patent is extended or adjusted under 35 U.S.C. 154(b) by 3 days.

(21) Appl. No.: 11/533,769

(22) Filed: Sep. 21, 2006

(65) Prior Publication Data

US 2007/0265443 A1    Nov. 15, 2007

(30) Foreign Application Priority Data

May 11, 2006   (TW)   ............................... 95116728 A

(51) Int. Cl.
C07D 409/14    (2006.01)
C07D 409/00    (2006.01)

(52) U.S. Cl. .................. 546/10; 544/225; 502/171; 546/2

(58) Field of Classification Search .............. 546/10, 546/2; 544/225; 502/171
See application file for complete search history.

(56) References Cited

OTHER PUBLICATIONS

"A low-cost, high-efficiency solar cell based on dye-sensitized colloidal TiO2 films", Brian O'Regan, Michael Grätzel, Nature 353, Oct. 24, 1991. pp. 737-740.

(Continued)

*Primary Examiner*—Charanjit S. Aulakh
(74) *Attorney, Agent, or Firm*—Jianq Chyun IP Office

(57) ABSTRACT

A photosensitizer dye is provided. The photosensitizer dye contains a Ru complex represented by the following formula (1):

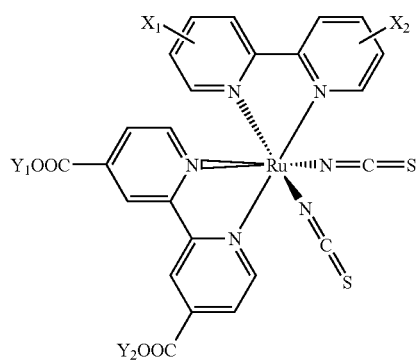

wherein $Y_1$ and $Y_2$ independently represent hydrogen atom (H), lithium (Li), sodium (Na) or tetra-alkyl ammonium groups (as represented by the following general formula (2)).

Formula (2):

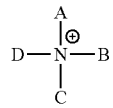

wherein A, B, C and D independently represents $C_mH_{2m+1}$ (m=1~6).

Wherein $X_1$ represents one of the following formulas (3)~(8) and $X_2$ represents H or a group the same as $X_1$, (3)

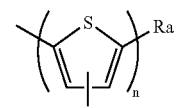

(4)

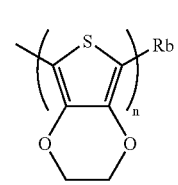

(5)

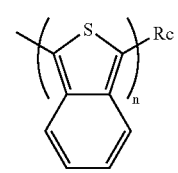

(6)

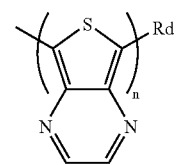

(7)

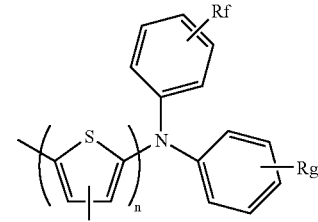

(8)

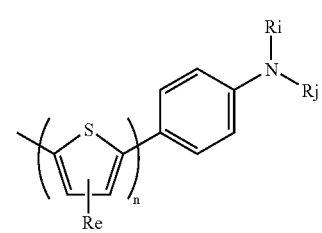

1 Claim, 2 Drawing Sheets

OTHER PUBLICATIONS

"Engineering of Efficient Panchromatic Sensitizers for Nanocrystalline TiO2-Based Solar Cells", Mohammad K. Nazeeruddin, Peter Péchy, Thierry Renouard, Shaik M. Zakeeruddin, Robin Humphry-Baker, Pascal Comte, Paul Liska, Le Cevey, Emiliana Costa, Valery Shklover, Leone Spiccia, Glen B. Deacon, Carlo A. Bignozzi, and Michael Grätzel, 2001 American Chemical Society 123, pp. 1613-1624.

"Stable new sensitizer with improved light harvesting for nanocrystalline dye-sensitized solar cells", Peng Wang ; Zakeeruddin Shaik M. ; Moser Jacques E. ; Humphry-Baker Robin ; Comte Pascal ; Aranyos Viviane ; Hagfeldt Anders ; Nazeeruddin Mohammad K. ; Grätzel Michael, 2004, vol. 16, No. 20, pp. 1806-1811.

"A High Molar Extinction Coefficient Sensitizer for Stable Dye-Sensitized Solar Cells", Peng Wang, Cédric Klein, Robin Humphry-Baker, Shaik M. Zakeeruddin, and Michael Grätzel, American Chemical Society 2005, 127, pp. 808-809.

"High Efficiency of Dye-Sensitized Solar Cells Based on Metal-Free Indoline Dyes", Tamotsu Horiuchi, Hidetoshi Miura, Kouichi Sumioka, and Satoshi Uchida, American Chemical Society 2004, 126, pp. 12218-12219.

PHOTOSENSITIZER DYE

CROSS-REFERENCE TO RELATED APPLICATION

This application claims the priority benefit of Taiwan application serial no. 95116728, filed on May 11, 2006. All disclosure of the Taiwan application is incorporated herein by reference.

BACKGROUND OF THE INVENTION

1. Field of Invention

The present invention relates to a solar cell material. More particularly, the present invention relates to a photosensitizer dye applicable in a dye-sensitized solar cell.

2. Description of Related Art

Along with the development of technology and economy, the use of energy (such as oil (petroleum), natural gas, coal and etc.) has caused pollution which leads to serious damages to the environment. Further, the supply of these polluting energies is coming to a close and the looming shortage of energy is a serious world-wide problem. Accordingly, many nations have started to develop and invest in cleaner and renewable energy sources.

Since solar energy is an unlimited and non-polluting energy source, it has been proposed and used as an alternative to the fossil fuels based energy to resolve the problems of pollution and energy shortage. Solar cell (or photovoltaic) which can convert solar energy directly into electricity is under intensive study.

Recently, Grätzel and O'Regan have proposed a new type of solar cell known as dye-sensitized solar cell (DSSC), which offers the prospect of an effective use of solar energy, and thus draws the attention of researchers from both academia and industry. Typically a dye-sensitized solar cell is constituted with four parts including an anode/cathode for providing a channel of current flow, a metal oxide (generally $TiO_2$) semiconductor for accepting and transporting electrons, a photosensitizer, and an electrolyte for transporting holes. The materials and the junctions of the four parts in the dye-sensitized solar cell play important roles on the efficiency of the cell. Most particularly, the photosensitizer (or dye) is critical in determining the efficiency of the dye-sensitized solar cell. Accordingly, it is essential to identify a dye that can provide good efficiency of the dye-sensitized solar cell. It is well known that having high absorption coefficient is one of the most important parameters for being a good photosensitizer.

SUMMARY OF THE INVENTION

In view of the foregoing, the present invention provides a series of photosensitizer dyes that have a high absorption coefficient. Further, the behavior of the light absorption spectrum of the photosensitizer dye of the present invention is similar to that of solar light. Accordingly, the conversion efficiency of sunlight to electricity of the dye-sensitized solar cell can be effectively improved.

The present invention provides a series of photosensitizer dyes, wherein the photosensitizer dyes are ruthenium (Ru) complexes represented by the following general formula (1):

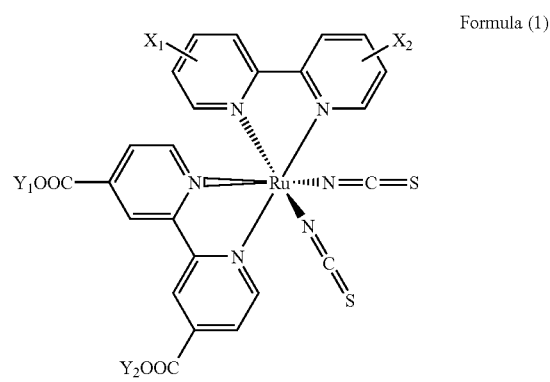

Formula (1)

wherein $Y_1$ and $Y_2$ independently represent hydrogen atom (H), lithium (Li), sodium (Na) or tetra-alkyl ammonium groups (as the following general formula (2)).

Formula (2)

wherein A, B, C and D independently represents $C_mH_{2m+1}$ (m=1~6). $X_1$ represents the following general formula (3), and $X_2$ represents hydrogen atom (H).

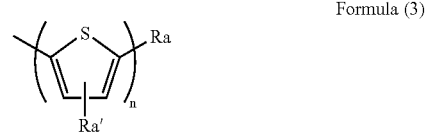

Formula (3)

wherein Ra, Ra' independently represents H and $C_mH_{2m+1}$ (m=1~15) or $OC_pH_{2p+1}$ (P=1~15), and n=1~4.

According to the photosensitizer dye of an embodiment of the present invention, $X_1$ and $X_2$ represents a same group and $X_2$ represents the above formula (3).

According to the photosensitizer dye of an embodiment of the present invention, $X_1$ represents the following general formula (4), and $X_2$ represents H,

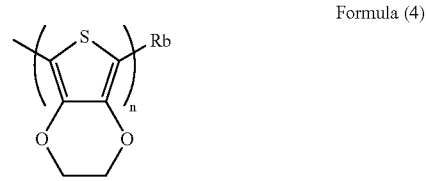

Formula (4)

wherein Rb represents H, $C_mH_{2m+1}$ (m=1~15) or $OC_pH_{2p+1}$ (P=1~15), and n=1~4. In one embodiment, $X_1$ and $X_2$ represents a same group and $X_2$ represents the above formula (4).

According to the photosensitizer dye of an embodiment of the present invention, $X_1$ represents the following general formula (5), and $X_2$ represents H,

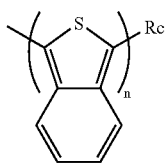

Formula (5)

wherein Rc represents H, $C_mH_{2m+1}$ (m=1~15) or $OC_pH_{2p+1}$ (P=1~15), and n=1~2. In one embodiment, $X_1$ and $X_2$ represents a same group and $X_2$ represents the above formula (5).

According to the photosensitizer dye of an embodiment of the present invention, $X_1$ represents the general formula (6), and $X_2$ represents H,

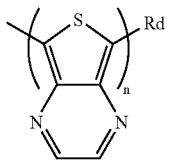

Formula (6)

wherein Rd represents H, $C_mH_{2m+1}$ (m=1~15) or $OC_pH_{2p+1}$ (P=1~15), and n=1~2. In one embodiment, $X_1$ and $X_2$ represents a same group and $X_2$ represents the above formula (6).

According to the photosensitizer dye of an embodiment of the present invention, $X_1$ represents the following general formula (7), and $X_2$ represents H,

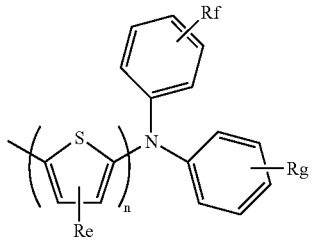

Formula (7)

wherein Re, Rf, Rg independently represents H, $C_mH_{2m+1}$ (m=1~15) or $OC_pH_{2p+1}$ (P=1~15), and n=1~2. In one embodiment, $X_1$ and $X_2$ represents a same group and $X_2$ represents the above formula (7).

According to the photosensitizer dye of an embodiment of the present invention, $X_1$ represents the following general formula (8), and $X_2$ represents H,

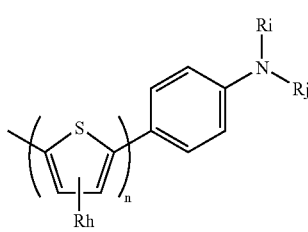

Formula (8)

wherein Rh, Ri, Rj independently represents H, $C_mH_{2m+1}$ (m=1~15) or $OC_pH_{2p+1}$ (P=1~15), and n=1~2. In one embodiment, $X_1$ and $X_2$ represents a same group and $X_2$ represent the above formula (8).

The ruthenium (Ru) complex photosensitizer dye of the present invention contains the groups of the above formulas (2) to (8). A higher absorption coefficient is thereby resulted. Further, the behavior of the absorption spectrum of the ruthenium (Ru) complex photosensitizer dye of the present invention is closer to that of the solar light. Moreover, the conversion efficiency of sunlight to electricity of the dye-sensitized solar cell (DSSC) fabricated with the ruthenium (Ru) complex photosensitizer dye of the present invention is higher than that of the DSSC fabricated with the conventional photosensitizer dyes. Further, besides being applicable in the fabrication of a dye-sensitized solar cell, the ruthenium (Ru)-complex photosensitizer dye of the present invention can also be used for detecting mercury ions.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
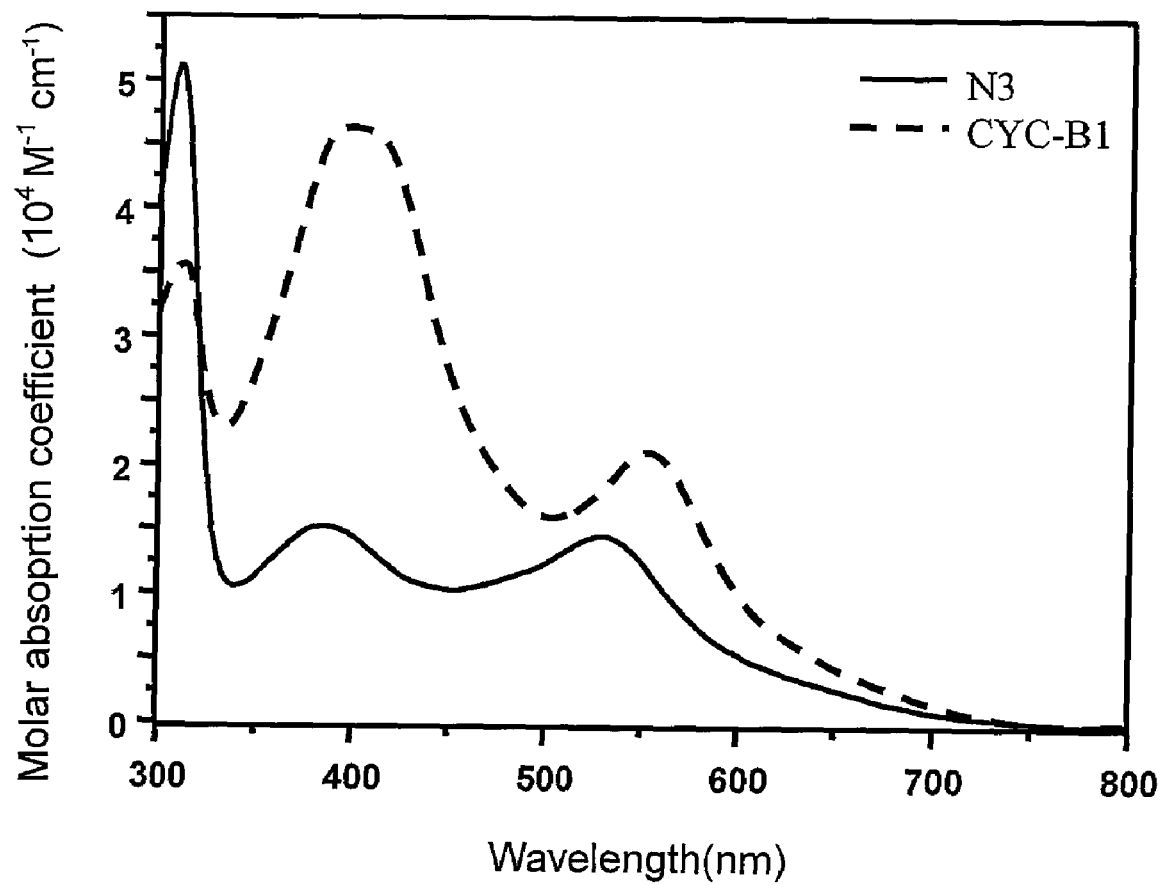
FIG. 1 presents the absorption spectra of the photosensitizer dye of the present invention (CYC-B1) and a conventional photosensitizer dye (N3).

The present invention provides a photosensitizer dye, wherein the photosensitizer dye contains a ruthenium (Ru)-complex having the following formula (1)

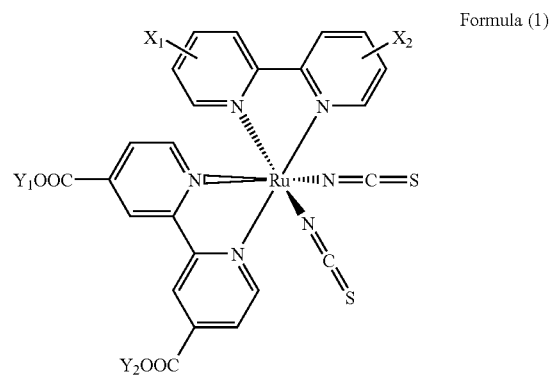

Formula (1)

In formula (1), wherein $Y_1$ and $Y_2$ independently represents hydrogen atom (14), lithium (Li), sodium (Na) or tetra-alkyl ammonium groups (as depicted in the following general formula (2)).

Formula (2)

wherein A, B, C and D independently represents $C_mH_{2m+1}$ m=1~6).

$X_1$ represents one of the following formulas (3) to (8). $X_2$ represents hydrogen atom (H).

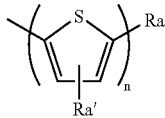

Formula (3)

wherein in formula (3), Ra, Ra' independently represent H and $C_mH_{2m+1}$ (m=1~15) or $OC_pH_{2p+1}$ (P=1~15), and n=1~4).

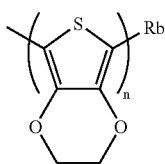

Formula (4)

wherein in formula (4), Rb represents H, $C_mH_{2m+1}$ (m=1~15) or $OC_pH_{2p+1}$ (P=1~15), and n=1~4.

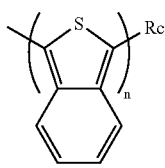

Formula (5)

wherein in formula (5), Rc represents H, $C_mH_{2m+1}$ (M=1~15) or $OC_pH_{2p+1}$ (P=1~15), and n=1~2.

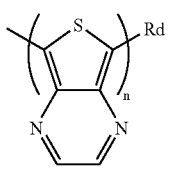

Formula (6)

wherein in formula (6), Rd represents H, $C_mH_{2m+1}$ (m=1~15) or $OC_pH_{2p+1}$ (P=1~15), and n=1~2.

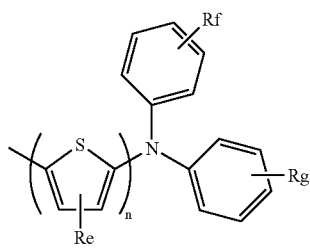

Formula (7)

wherein in formula (7), Re, Rf, Rg independently represent H, $C_mH_{2m+1}$ (m=1~15) or $OC_pH_{2p+1}$ (P=1~15), and n=1~2.

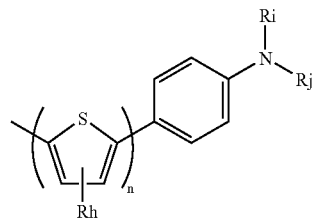

Formula (8)

wherein in formula (8), Rh, Ri, Rj independently represent H, $C_mH_{2m+1}$ (m=1~15) or $OC_pH_{2p+1}$ (P=1~15), and n=1~2.

In another embodiment, the photosensitzer dye of the present invention further includes Y1, Y2, $X_1$ and $X_2$ in formula (1), where $Y_1$ represents hydrogen atom (H), lithium (Li), sodium (Na) or tetra-alkyl ammonium groups (as depicted in the general formula (2)), and $Y_2$ represents hydrogen atom (H) or the same group as $Y_1$.

$X_1$ and X2 represent the same group, and $X_2$ representing one of the above formulas (3) to (8).

Since the ruthenium (Ru) complex photosensitizer dye of the present invention contains the groups of the forgoing formulas (2) to (8), the behavior of the light absorption spectrum of the ruthenium (Ru) complex photosensitizer dye of the present invention is very close to that of solar light. Further, the ruthenium (Ru) complex photosensitizer dye has a higher absorption coefficient. A higher absorption coefficient suggests that the ruthenium (Ru) complex photosensitizer dye of the present invention has a stronger capability to produce electron-hole pairs. In other words, with the application of the ruthenium (Ru) complex photosensitizer dye of the present invention in a dye-sensitized solar cell (DSSC), the DSSC can effectively convert the received sunlight into electricity.

Moreover, since the ruthenium (Ru)-complex photosensitizer dye of the present invention contains the groups of the above formulas (2) to (8), the energy level of the ruthenium (Ru) complex photosensitizer dye of the present invention is compatible with the redox potential of the mediator and the conductive band energy of the semiconductor of a typical DSSC. Hence, the resulting dye-sensitized solar cell (DSSC) has high light-to-electricity conversion efficiency. In order to effectively transport electrons and to minimize energy loss during the process, it is essential for the potential energy level of the excited state of the photosensitizer dye to be compatible with the potential energy level of the conductive band of the metal oxide material (for example, titanium dioxide, $TiO_2$). Moreover, it is necessary for the redox potential of the photosensitizer dye (the energy level of HOMO) to be lower than the redox potential of the electrolytes (for example, iodide ions). Accordingly, the photosensitizer dye can recover the lost electrons. The physical properties of the ruthenium (Ru) complex photosensitizer dye of the present invention will be described as follows.

The following embodiment describes the synthesis of the ruthenium (Ru) complex photosensitizer dye of the present invention. It should be appreciated that the following description should be regarded as illustrative rather than restrictive.

THE EMBODIMENT

The chemical compound (depicted as CYC-B1), in which Y1 and Y2 in formula (1) are H, while $X_1$ and $X_2$ in formula (1) are of a same group, $X_2$ represents formula (3), Ra in formula (3) represents $C_8H_{17}$, Ra' represents H and n=2, is used as an example to illustrate the synthesis of the ruthenium (Ru) complex photosensitizer dye of the present invention.

Process Flow 1:

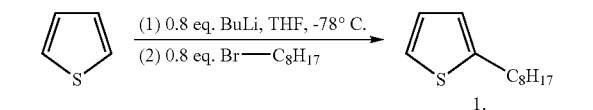

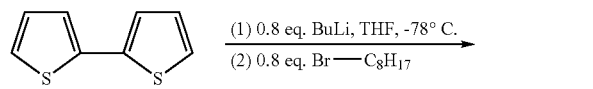

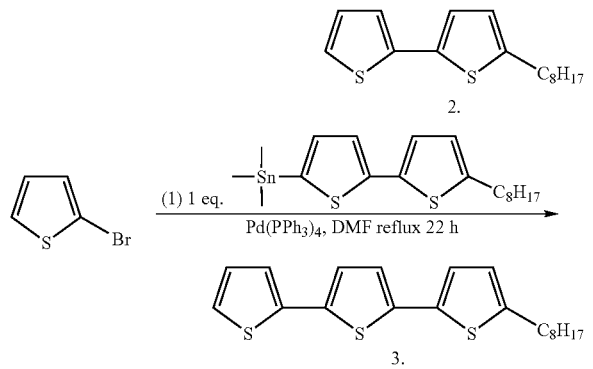

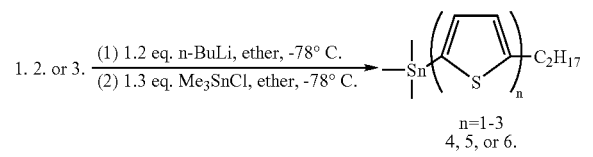

n=1-3
4, 5, or 6.

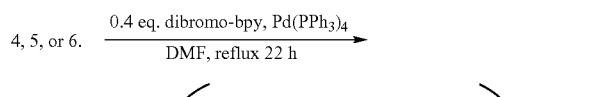

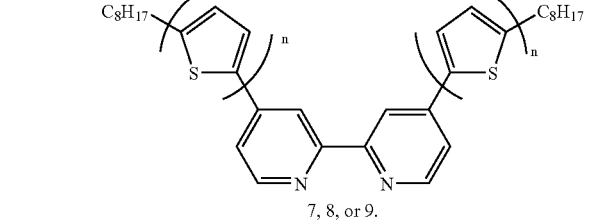

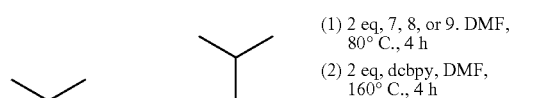

-continued

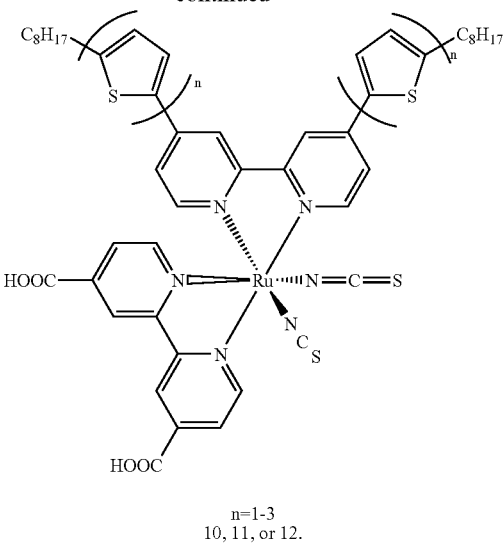

n=1-3
10, 11, or 12.
(THF = tetrahydrofuran, DMF = dimethylformamide)

The process is commenced by placing about 3 g of bithiophene in a round bottom flask with a side arm (for introducing an inert gas), followed by adding an anhydrous tetrahydrofuran to dissolve the bithiophene. The temperature of the solution is then lowered to −78° C. (using liquid nitrogen plus ethanol as coolant). Thereafter, about 5.8 ml of n-butyl lithium (n-BuLi) (2.5 M, dissolved in hexane) is gradually drop-added to the solution. After the temperature of the solution has returned to room temperature, the solution is continuously mixed for about 15 minutes. After this, 2.5 ml of 1-bromooctane (Br—$C_8H_{17}$) is added, and the solution is continuously stirred for about 10 hours. The reaction was carried out under the inert gas all the time. After a predetermined reaction time is reached, deionized water is added to terminate the reaction. An extraction is performed by adding ether to the solution. An organic layer is then collected. Another extraction of the organic layer is performed using a saturated sodium hydrogen carbonate aqueous solution, deionized water and a saturated sodium chloride solution, respectively. The resulting crude product is then purified using column chromatography (eluent is hexane) to obtain an intermediate product octylbithiophene (the yield is about 65.1%).

Thereafter, about 3.4 g of octylbithiophene is dissolved in an anhydrous THF. The temperature of the solution is further lowered to −78° C. using coolant, followed by gradually drop-adding 5.86 ml of n-BuLi (2.5M, dissolved in hexane) to the solution. After this, the temperature of the solution is returned to room temperature, and the solution is stirred for about two hours. The temperature of the solution is again lowered to −78° C. Then, about 3.16 g of trimethyltin chloride (dissolved in an appropriate amount of THF) is added to the solution. After the temperature of the solution returns to room temperature, the solution is continuously stirred for about 12 hours. Thereafter, deionized water is added to terminate the reaction, and an extraction is performed using a saturated sodium hydrogen carbonate aqueous solution, deionized water and a saturated sodium chloride solution, respectively. An organic layer is collected, and the solvent is removed to obtain about 4.76 g of the crude product, which is 8-(trimethyltin)-2-octylbithiophene (the yield is about 88.5%).

Thereafter, about 0.63 g of 8-(trimethyltin)-2-octylbithiophene and about 0.2 g of 4-4'-dibromo-2,2'-bipyridine (the method of synthesis can be referred to I. Murase, Nippon Kagaku Zasshi, 1956, 77, 682; G. Mnerker and F. H. Case, J. Am. Chem. Soc., 1958, 80, 2745; and D. Wenkert and R. B. Woodward, J. Org. Chem., 1983, 48, 283) are dissolved in 25 ml of anhydrous dimethylformamide (DMF). About 0.089 g of tetrakis(triphenylphosphine) palladium is added as a catalyst. After this, the solution is heated and refluxed for about 22 hours. When the temperature of the solution returns to room temperature, about 5 wt % of ammonium chloride aqueous solution is added to the solution to terminate the reaction. After performing an extraction using dichloromethane, an organic layer is collected. Thereafter, another extraction of the organic layer is conducted using a sodium hydrogen carbonate aqueous solution, deionized water and a saturated sodium chloride aqueous solution, respectively. After removing the solvent of the organic layer, a crude product is obtained. The crude product is purified by a Soxhlet extractor (using hexane to remove the impurity and then ethyl acetate to extract the product). Ethyl acetate was removed with a vacuum system, and about 0.237 g of ligand-1 is remained (the yield is about 55.0%).

The Ru-complex was prepared by dissolving 0.3173 g of [RuCl$_2$(p-cymene)]$_2$ and 0.734 g of ligand-1 in 30 ml of the anhydrous DMF. The solution is then heated to about 80° C. for about 4 hours. After this, 0.2530 g of dcbpy (4-4'-dicarboxyl-2,2'-bipyridine) is added to the solution, followed by heating the solution to about 160° C. The solution is allowed to react for another 4 hours. It is worthy to note that the above chemical reactions must be conducted in the dark to prevent the generation of isomers caused by light. Thereafter, an excessive amount of NH$_4$NCS is added to the solution, and the reaction is continued for about 5 hours at a temperature about 130° C. After the reaction is completed, the solution was concentrated by removing some of the solvent DMF using a vacuum system. Water was added to the solution to precipitate the product. The solid substance was obtained by vacuum filtration. Deionized water, sodium hydroxide solution at pH 12 and ether respectively was used to wash the solid crude product. The crude product is then dissolved in methanol. After passing the solution through a column (methanol being the eluent), a dark color section of the solution is collected. After a majority of the solvent is removed, few drops of a 0.01M nitric acid aqueous solution were added to the solution, a precipitation of about 0.4838 g of the product (CYC-B1) is obtained. The yield of CYC-B1 is about 39.9%.

The following description is directed to the measuring method of the absorption coefficient of the photosensitizer dye of the present invention. A comparison between the absorption coefficient of CYC-B1 of the present invention and that of a conventional photosensitizer dye is also provided.

According to the measuring method of the absorption coefficient of the photosensitizer dye of the present invention, a photosensitizer dye solution of known concentration is first provided. An appropriate amount of the solution is then placed in a quartz sample cell, the sample cell is then placed in a UV/Vis Spectrophotometer for the analysis. The absorption coefficient can be calculated by using the Beer's law (A=$\epsilon$bc, A: absorbance; $\epsilon$: absorption coefficient; b: beam path; c: concentration of the sample). The absorption coefficient of the photosensitizer dye of the present invention (CYC-B1) is compared with the absorption coefficient of the various conventional photosensitizer dyes, and the results are summarized in Table 1.

The conventional photosensitizer dyes, "N3", "Black dye", "Z-910", "K-19", and "K-8", listed in Table 1 are respectively disclosed by M. Grätzel, J. Photochem. A, 2004, 164, 3, M. K. Nazeeruddin et al., J. Am. Chem. Soc. 1993, 115, 6382, M. K. Nazeeruddin et al., J. Am. Chem. Soc., 2001, 123, 1613, M. K. Nazeeruddin et al., J. Am. Chem. Soc., 2001, 123, 1613, Michael Grätzel et al., J. Am. Chem. Soc, 2005, 127, 808, and C. Klein et al., Inorg. Chem., 2005, 44, 178.

TABLE 1

| Photosensitizer Dye | CYC-B1 | N3 | Black dye | Z-910 | K-19 | K-8 |
|---|---|---|---|---|---|---|
| The absorption coefficient of the $\lambda$max with the smallest energy (*10$^{-3}$ M$^{-1}$ cm$^{-1}$) | 21.2 | 14.5 | 7.48 | 16.8 | 18.2 | 17.4 |

As shown in Table 1, the absorption coefficient of the CYC-B1 dye of the present invention is higher than those of the conventional dyes. Accordingly, due to the presence of the special groups of the foregoing formulas (2) to (8) in the ruthenium (Ru) complex photosensitizer dye of the present invention, the absorption coefficient of the resulting photosensitizer dye is higher. Therefore, the application of the ruthenium (Ru) complex photosensitizer dye of the present invention in a dye-sensitized solar cell will result in higher energy conversion efficiency.

Figure 2:
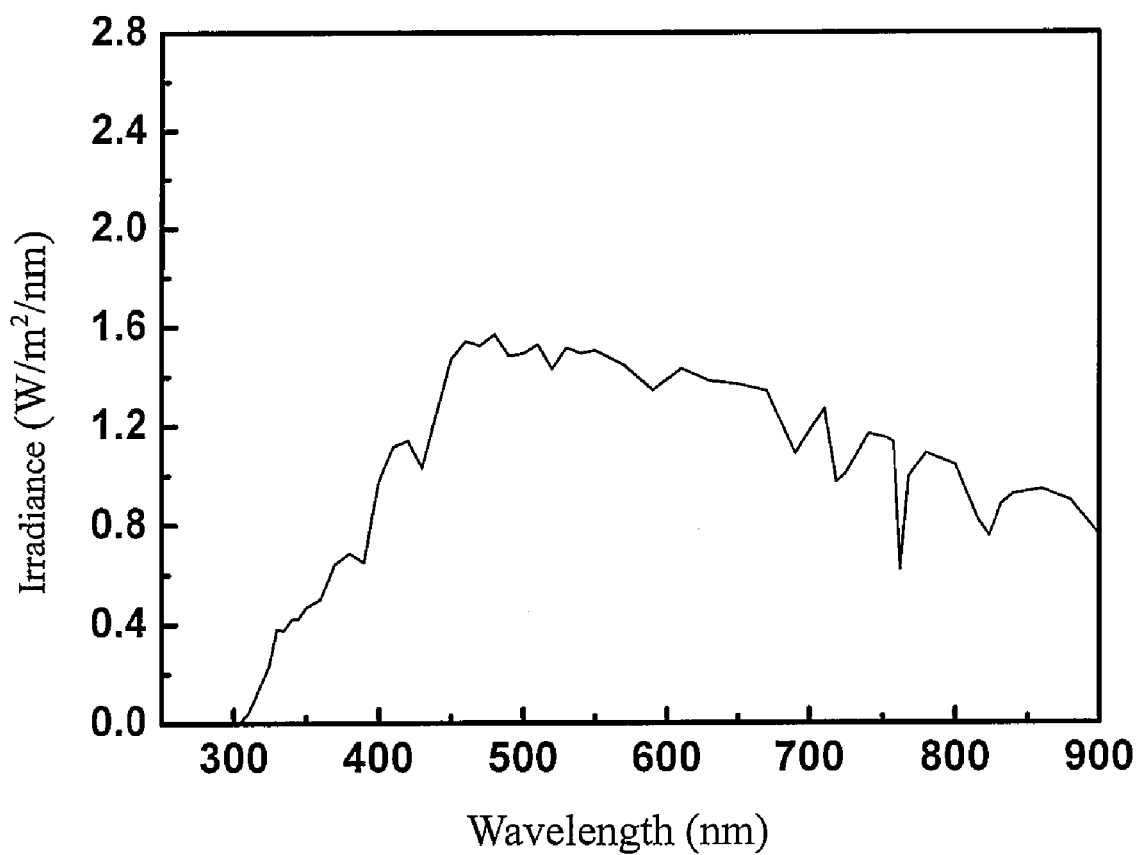
FIG. 2 presents the absorption spectrum of solar light.

Additionally, the absorption spectra of the CYC-B1 and N3 dyes (as shown in FIG. 1) are respectively compared with the solar spectrum (as shown in FIG. 2), which is provided in Annual Book of ASTM Standard, G159-98 Standard tables for references solar spectral irradiance at air mass 1.5: direct normal and hemispherical for a 37° tilted surface, Vol. 14.04 (2003). As shown in FIGS. 1 & 2, the behavior of the absorption spectrum of CYC-B1 is closer than that of N3 to the solar spectrum. Accordingly, it is more desirable to apply the ruthenium (Ru) complex photosensitizer dye of the present invention in a dye-sensitized solar cell because higher energy conversion efficiency can be obtained.

The following description is directed to the fabrication method of a dye-sensitized solar cell, wherein the photosensitizer is formed with the ruthenium (Ru)-complex photosensitizer dye of the present invention. The efficiency of the resulting device is also provided.

The fabrication method of a dye-sensitized solar cell using CYC-B1 dye of the present invention as the photosensitizer includes first soaking a titanium dioxide (TiO$_2$) electrode in a CYC-B1-containing solution for a period of time. The CYC-B1 dye attaches to the surface of the TiO$_2$ electrode by a self-assembly manner. Thereafter, the TiO$_2$ electrode is removed from the CYC-B1-containing solution. The TiO$_2$ electrode is rinsed with a solvent and dried, followed by sealing with an epoxy. The intervening space inside the epoxy is filled with an electrolyte solution. After sealing the injection opening, the preparation of a dye-sensitized solar cell is completed. Subsequent to the fabrication of a dye-sensitized solar cell using the CYC-B1 dye of the present invention for the photosensitizer, the voltage, the current density and the energy conversion efficiency of the solar cell are measured and the results are summarized in Table 2.

Similarly, the same method is used to fabricate a dye-sensitized solar cell using N3 as the photosensitizer dye. The voltage, the current density, and the energy conversion efficiency of the N3-sensitized solar cell are measured and the results are also summarized in Table 2.

TABLE 2

| Photosensitizer Dye | The absorption coefficient of the λmax with the smallest energy (*10$^{-3}$ M$^{-1}$ cm$^{-1}$) | Short Circuit Current Density, Isc (mA/cm$^2$) | Open Circuit Voltage, Voc (V) | Energy Conversion Efficiency, η (%) |
|---|---|---|---|---|
| CYC-B1 | 21.2 | 23.9 | 0.65 | 8.5 |
| N3 | 14.5 | 21.32 | 0.55 | 7.7 |

As shown in Table 2, using CYC-B1 as a dye to fabricate the dye-sensitized solar cell, the energy conversion efficiency is about 8.5%, whereas the energy conversion efficiency is only about 7.7% for the N3-sensitized solar cell fabricated with the same method. It is obvious from the information provided in Table 2 that because of the ruthenium (Ru) complex photosensitizer dye of the present invention contains the special groups; therefore the energy conversion efficiency is higher than those of the conventional photosensitizer dyes.

Besides applying the ruthenium (Ru) complex photosensitizer dye in the fabrication of a dye-sensitized solar cell, the ruthenium (Ru) complex photosensitizer dye of the present invention was also known to be used in the detection of mercury ions.

Accordingly, due to the presence of the special groups the ruthenium (Ru) complex photosensitizer dye of the present invention has the highest absorption coefficient when compared with other dyes in the literature. Moreover, the behavior of the absorption spectrum of the ruthenium (Ru) complex photosensitizer dye is closer to that of the solar absorption spectrum. Therefore, the energy conversion efficiency of the DSSC fabricated using the ruthenium (Ru)-complex photosensitizer dye of the present invention can be higher than that of the DSSCs fabricated using the conventional dyes. Furthermore, the ruthenium (Ru) complex photosensitizer dye of the present invention can be applied in other field besides in the field of a dye-sensitized solar cell, for example, in the detection of mercury ions, etc.

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. A photosensitizer dye for a dye sensitized solar cell, wherein the photosensitizer dye is a ruthenium (Ru) complex represented by the following general formula (1),

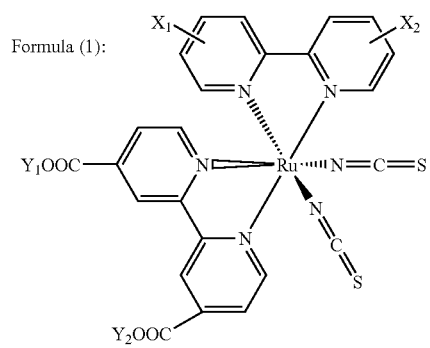

Formula (1):

wherein $Y_1$ and $Y_2$ independently represent hydrogen atom (H), lithium (Li), sodium (Na) or tetra-alkyl ammonium groups represented by the following general formula (2), Formula (2)

$$D-\overset{A}{\underset{C}{N^{\oplus}}}-B$$

wherein A, B, C and D independently represent $C_mH_{2m+1}$ (m=1~6), and wherein $X_1$ represents one of the following general formulas of formula (3), formula (4), formula (5), formula (6), formula (7) and formula (8), and $X_2$ represents hydrogen atom (H) or the same group as $X_1$, Formula (3):

wherein Ra, Ra' are independently selected from the group consisting of H, $C_mH_{2m+1}$ (m=1 to 15) and $OC_pH_{2p+1}$ (P=1 to 15), and n=1 to 4, Formula (4):

wherein Rb is selected from the group consisting of H, $C_mH_{2m+1}$ (m=1 to 15) and $OC_pH_{2p+1}$ (P=1 to 15), and n=1 to 4, Formula (5):

wherein Rc is selected from the group consisting of H, $C_mH_{2m+1}$ (m=1 to 15) and $OC_pH_{2p+1}$ (P=1 to 15), and n=1 to 2, Formula (6):
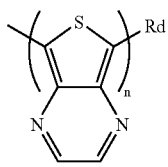
wherein Rd is selected from the group consisting of H, $C_mH_{2m+1}$ (m=1 to 15) and $OC_pH_{2p+1}$ (P=1 to 15), and n=1 to 2,
Formula (7):
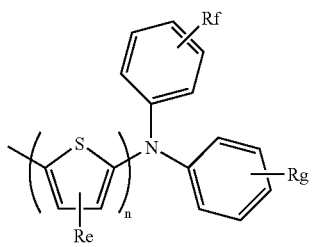
wherein Re, Rf, Rg are independently selected from the group consisting of H, $C_mH_{2m+1}$ (m=1 to 15) and $OC_pH_{2p+1}$ (P=1 to 15), and n=1 to 2,
Formula (8):
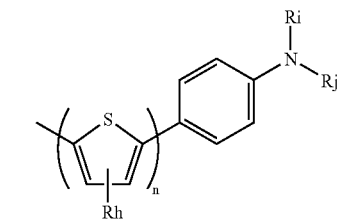
wherein Ri, Rj, Rh are independently selected from the group consisting of H, $C_mH_{2m+1}$ (m=1 to 15) and $OC_pH_{2p+1}$ (P=1 to 15), and n=1 to 2.
* * * * *